United States Patent
Mcgregor et al.

(10) Patent No.: US 9,730,645 B2
(45) Date of Patent: Aug. 15, 2017

(54) METHOD AND SYSTEM FOR DETERMINING HRV AND RRV AND USE TO IDENTIFY POTENTIAL CONDITION ONSET

(76) Inventors: Carolyn Patricia Mcgregor, Brooklin (CA); Christina Anne Catley, Ottawa (CA); Andrew Gibson James, Toronto (CA)

( * ) Notice: Subject to any disclaimer, the term of this patent is extended or adjusted under 35 U.S.C. 154(b) by 519 days.

(21) Appl. No.: 14/005,107

(22) PCT Filed: Mar. 19, 2012

(86) PCT No.: PCT/CA2012/000243
§ 371 (c)(1),
(2), (4) Date: Nov. 4, 2013

(87) PCT Pub. No.: WO2012/122637
PCT Pub. Date: Sep. 20, 2012

(65) Prior Publication Data
US 2014/0052007 A1 Feb. 20, 2014

Related U.S. Application Data

(60) Provisional application No. 61/453,905, filed on Mar. 17, 2011.

(51) Int. Cl.
*A61B 5/0402* (2006.01)
*A61B 5/00* (2006.01)
(Continued)

(52) U.S. Cl.
CPC .......... *A61B 5/7282* (2013.01); *A61B 5/0022* (2013.01); *A61B 5/0205* (2013.01);
(Continued)

(58) Field of Classification Search
CPC ..... A61B 5/0022; A61B 5/0205; A61B 5/024; A61B 5/0402; A61B 5/0816;
(Continued)

(56) References Cited

U.S. PATENT DOCUMENTS

2005/0197865 A1\* 9/2005 Jordan ................ G06F 19/3431
705/3

FOREIGN PATENT DOCUMENTS

WO 2009043144 A1 4/2009
WO 2011009211 A1 1/2011

OTHER PUBLICATIONS

Chung et al, Applying Temporal Abstraction in Clinical Databases, 2007 IEEE International Conference on Research, Innovation and Vision for the Future, 192-199.\*

(Continued)

*Primary Examiner* — Jacqueline Cheng
*Assistant Examiner* — Angeline Premraj
(74) *Attorney, Agent, or Firm* — Norton Rose Fulbright Canada LLP

(57) ABSTRACT

The present disclosure relates to a method and system for identifying potential condition onset based upon a combination of Heart Rate Variability (HRV), Respiratory Rate Variability (RRV) and/or confounding factors. The present method and system may involve data collection, a temporal abstraction (TA)-based approach, and data analysis to identify potential condition onset in patients. The present method and system may generate and amend a classification scheme to be operable to determine that a patient is facing potential condition onset. The present method and system may further be operable to provide clinical decision making support. Embodiments of the present method and system may be operable to identify trends, such as temporal patterns, and to undertake a variety of analyses of collected and/or TA data to provide indicators, and determinations of potential condition onset in patients. As an example, the present method and system may be applied to identify potential condition onset of sepsis in infant patients.

18 Claims, 7 Drawing Sheets

(51) Int. Cl.
*A61B 5/0205* (2006.01)
*A61B 5/08* (2006.01)
*G06F 19/00* (2011.01)
*A61B 5/024* (2006.01)

(52) U.S. Cl.
CPC .......... *A61B 5/0402* (2013.01); *A61B 5/4839* (2013.01); *A61B 5/4848* (2013.01); *A61B 5/024* (2013.01); *A61B 5/0816* (2013.01); *G06F 19/345* (2013.01)

(58) Field of Classification Search
CPC ... A61B 5/4839; A61B 5/4848; A61B 5/7282; G06F 19/345
See application file for complete search history.

(56) References Cited

OTHER PUBLICATIONS

Shahar, A framework for knowledge-based temporal abstraction, 1997, Artificial Intelligence, 70:79-133.*

State Intellectual Property Office of the People's Republic of China, Second Office Action dated Aug. 5, 2015 issued on corresponding Chinese application 201280022727.9.

State Intellectual Property Office of the People's Republic of China, First Office Action dated Jan. 5, 2015 issued on Chinese Application No. 201280022727.9, P.R. China.

Stacey, M. et al, "An architecture for multi-dimensional temporal abstraction and its application to support neonatal intensive care", Proceedings of the 29th Annual International Conference of the IEEE EMBS, Lyon, France, Aug. 23-26, 2007, pp. 3752-3756.

Patent Cooperation Treaty, International Search Report and Written Opinion dated Aug. 23, 2012 issued on International Application No. PCT/CA2012/000243.

Bressan, N. et al., "Trends and Opportunities for Integrated Real Time Neonatal Clinical Decision Support", Proceedings of the IEEE-EMBS International Conference on Biomedical and Health Informatics (BHI2012), Hong Kong and Shenzhen, China, Jan. 2-7, 2012, pp. 687-690.

Blount, M. et al., "Real-Time Analysis for Intensive Care: Developments and Deployment of the Artemis Analytic System", IEEE Engineering in Medicine and Biology Magazine, Mar./Apr. 2010, pp. 110-118.

Catley, C. et al. "Extending CRISP-DM to Incorporate Temporal Data Mining of Multidimensional Medical Data Streams: A Neonatal Intensive Care Unit Case Study", 22nd IEEE International Symposium on Computer-Based Medical Systems (CMBS), Aug. 2-5, 2009, pp. 1-5.

Stacey, M. et al., "Temporal abstraction in intelligent clinical data analysis: A survey", Artificial Intelligence in Medicine (2007) 39, pp. 1-24.

State Intellectual Property Office of China, Office Action for CN Application No. 2012800227279 dated May 3, 2016.

IP Australia, Patent Examination Report No. 1 dated Aug. 31, 2015 issued on Australian Patent Application No. 2012228898.

Office Action for corresponding GB Patent Application No. 1318320.7 dated Feb. 15, 2016.

Intellectual Property Office, Examination Report for GB Application No. 1319320.7 dated Aug. 16, 2016.

* cited by examiner

28

30

METHOD AND SYSTEM FOR DETERMINING HRV AND RRV AND USE TO IDENTIFY POTENTIAL CONDITION ONSET

FIELD OF INVENTION

This invention relates in general to the field of identifying potential condition onset and more particularly to a method and system for identifying potential condition onset based upon a combination of Heart Rate Variability (HRV), Respiratory Rate Variability (RRV) and/or confounding factors

BACKGROUND OF THE INVENTION

Current algorithmic approaches for the early identification of sepsis rely on processing data streams with a high level of complexity and granularity. For example, one prior art method derives the instantaneous heart rate from electrocardiogram (ECG) waveform data acquired at 1000 readings a second. The prior art data processing algorithms are inherently complex, often appearing as a black box to end-users. An increasing number of studies indicate that properly designed and effectively used Clinical Decision Support Systems (CDSSs) have the ability to improve quality of patient care. As an example, such a study is described in: Wright A, Sittig D F, Ash J S, Sharma S, Pang J E, Middleton B. Clinical decision support capabilities of commercially-available clinical information systems. J Am Med Inform Assn. 2009; 16(5):637-44.

The black box approach of the prior art raises concerns about the possible negative effects of CDSSs, including: potential de-skilling effects if system users do not understand how results were generated; a lack of flexibility and overly prescriptive outcomes; promoting over-reliance on software applications, which is a risk in the event of system failure when systems provide risk indexes and clinicians do not know how they were derived; and difficulty in evaluating outcomes. Such possible negative effects are described in: Open Clinical. Potential benefits and drawbacks of the use of CDSSs; Factors which may help determine the successful use of CDSSs in clinical practice [Internet]. 2005. Available from: http://www.openclinical.org/dssSuccessFactors.html.

Additionally, in many prior art Neonatal Intensive Care Units (NICUs) it is not possible to acquire and store data at a high enough sampling frequency to support the Heart Rate Variability (HRV) algorithms. These limitations may explain the small number of research level HRV analysis systems that translate from 'bench to bedside' and challenges associated with enabling real-time support in clinical practice.

HRV is the oscillation in the interval between consecutive heart beats, as is described in Task Force of the European Society of Cardiology the North American Society of Pacing Electrophysiology. Heart rate variability standards of measurement, physiological interpretation and clinical use. Circulation. 1996; 93:1043-1065. The potential medical application of monitoring HRV in newborn infants arises from the observation that abnormal HRV is associated with neonatal morbidity and mortality; therefore, HRV may have the potential to provide a non-invasive diagnostic tool for clinically important conditions of the newborn infant. This possibility is discussed in: de Beer N A M, Andriessen P, Berendsen R C M, Oei S G, Wijn P F F, Bambang Oetomo S B. Customized spectral band analysis compared with conventional Fourier analysis of heart rate variability in neonates. Physiol Meas. 2004; 25(6):1385-1395.

Reduced HRV in neonates has been associated with respiratory distress syndrome (as discussed in Aarimaa T, Oja R, Antila K, Valimaki 1. Interaction of heart rate and respiration in newborn babies. Pediatr Res. 1988; 24(6):745-750), birth asphyxia and intraventricular hemorrhage (as discussed in, Divon M Y, Winkler H, Yeh S Y, Platt L D, Lamger O, Merkatz I R. Diminished respiratory sinus arrhythmia in asphyxiated term infants. Am J Obstet Gynecol. 1986; 155(6):1263-6 and Prietsch V, Knoepkeb U, Obladenc M. Continuous monitoring of heart rate variability in preterm infants. Early Hum Dev. 1994; 37(2):117-131). In addition, substantial research has shown that abnormal heart rate characteristics precede the subtle clinical features of Late Onset Neonatal Sepsis (LONS). Previous prior art work on early detection of sepsis has described mathematical processing of the instantaneous Heart Rate (HR) to obtain characteristics such as HRV (as discussed in Griffin M P, Lake D E, Moorman J R. Heart rate characteristics and laboratory tests in neonatal sepsis Pediatrics. 2005; 115(4): 937-41; Griffin M P, O'Shea T M, Bissonette E A, Harrell F E, Lake D E, Moormman J R. Abnormal heart rate characteristics preceding neonatal sepsis and sepsis-like illness. Pediatr Res. 2003; 53(6):920-6; and Griffin M P, Moornian R. Using novel heart rate analysis. Pediatrics. 2001; 107(1): 97-104) and HR decelerations (as discussed in Flower A A, Moorman J R, Lake D E, Delos J B. Periodic heart rate decelerations in premature infants. Experimental Biology and Medicine. 2010; 235(4):531-8).

Newborn infants, especially premature infants, are very susceptible to infectious pathogens (as discussed in (Ganatra H a, Stoll B J, Zaidi A K M. International perspective on early-onset neonatal sepsis. Clin Perinatol. 2010:37(2):501-523). Early diagnosis of sepsis can be important because infants are often diagnosed only when seriously ill which decreases the probability for prompt, complete recovery with antibiotic therapy. Diagnosing neonatal sepsis is a challenging problem because it does not conform to a 'typical' presentation (as is discussed in Gwadry-Sridhar F, Lewden B, Mequanint 5, Bauer M_Comparison of analytic approaches for determining variables—a case study in predicting the likelihood of sepsis. Proceedings of HEALTH-INF; 2009: Porto, Portugal: 90-96) and the signs of sepsis in the neonate are often nonspecific (as is discussed in Griffin M P, Lake D E, M O T, Moorman J R. Heart rate characteristics and clinical signs in neonatal sepsis. Pediatr Res. 2007; 61(2):222-227, and Beck-Sague C M, Azimi P, Fonseca S N, Baltimore R S, Powell D A, Bland L A, et al. Bloodstream infections in neonatal intensive care unit patients: results of a multicenter study. Pediatr Infect Dis J. 1994; 13(12):1110-1116).

There are two sepsis classifications; early-onset neonatal sepsis (EONS) and LONS, where EONS is typically defined as sepsis occurring within the first three or 7 days after birth and LONS occurring as early as four days after birth and as late as 28 days after birth; for the purpose of this study we use the definition that EONS is sepsis acquired in the first 4 days of life and LONS refers to sepsis acquired on or after the fifth day of life. Studies have shown that LONS occurs in approximately 10% of all neonates and in more than 25% of very low birth weight infants who are hospitalized in NICUs.

In 2001, Griffin and Moorman published novel results based on monitoring neonates with risk factors for acquiring LONS. They concluded that patients that developed sepsis and sepsis-like illness had reduced HRV and short HR decelerations for up to 24 hours preceding clinical deterioration (as discussed in Griffin M P, Moornian R. Using novel heart rate analysis. Pediatrics. 2001; 107(1):97-104). Further prior art studies found that these heart rate characteristics (HRC) added significantly to the predictive information of birth weight, gestational age, and days of age. Further refinement to these studies added an illness severity score; combined this score with HRCs; and used multivariate logistic regression to create a risk assessment card for sepsis. A combined model based on their logistic based approach and k-nearest neighbour analysis yielded a receiver operator characteristic of 0.87 (as discussed in Xiao Y, Griffin M P, Lake D E, Moorman J R. Nearest-neighbor and logistic regression analyses of clinical and heart rate characteristics in the early diagnosis of neonatal sepsis. Med Decis Making. 2010; 30(2):25866). These findings indicate that subtle changes, which may not be apparent through manual recordings at regular intervals, can be important in detecting the onset of sepsis in neonates. However, in the majority of NICUs, current information management practices do not make provision for storage and analysis of real-time data streams, with manual recordings every 30-60 minutes being the norm.

Although infants in the NICU frequently receive medications that affect the nervous system, relatively little has been published on the impact of these drugs on neonatal HRV and possible associated limitations in using HRV as an early indicator of LONS. In de Beer N A M, Andriessen P, Berendsen R C M, Oei S G, Wijn P F F, Bambang Oetomo S B. Customized spectral band analysis compared with conventional Fourier analysis of heart rate variability in neonates. Physiol Meas. 2004; 25(6):1385-1395, the authors demonstrate that atropine, which is a muscarinic receptor antagonist that is used to inhibit the effects of excessive vagal activation on the heart, resulting in large variations in HRV before and after atropine. While it is known that HRV occurs at the same frequency as respiration and is under the control of the parasympathetic branch of the autonomic nervous system (as is discussed in Brown L. Heart rate variability in premature infants during feeding. Biological Research for Nursing. 2007; 8(4):283-93), the relationship between HRV and RRV, in the presence of confounders, such as narcotics and other drugs, is not clear.

Prior art methods focus upon the relationship between HRV and specific clinical conditions, For example, Loforte et al studied HRV and the association between the heart's RR-wave intervals and the spontaneous respiration in a selected population of sick premature infants and found that lower relationship values were strongly associated with sepsis (Loforte R, Carrault G, Mainardi L, Beuche A. Heart rate and respiration relationships as a diagnostic tool for late onset sepsis in sick preterm infants. Computers in Cardiology. 2006; 33:737-740). The Loforte paper hypothesizes that exploration of HRV and respiration relationships may provide an indicator of infection in premature newborns.

As another example, Saria et al. developed an individualized risk scoring system for preterm, low birth weight infants (≤34 weeks gestation, birth weight ≤2000 g) using three non-invasive physiological parameters-heart rate, respiratory rate, and oxygen saturation-acquired during the first three hours of life together with gestational age and birth weight to predict morbidity, including infection (Saria S, Rajani A K, Gould J, Koller D, Penn A A. Integration of early physiological responses predicts later illness severity in preterm infants. Sci Transl Med. 2010; 2(48):1-8). The Saria paper makes a comparison with an electronic Apgar score, as it is predictive of future illness severity. This work calculated HRV and RRV using mean values plus baseline and residual variability signals. However, the authors stated that they selected the first three hours of life because this time period was less likely to be confounded by medical interventions, such as surgery, narcotics or other drugs.

Additional relevant prior art includes: Adlassnig K P, Combi C, Das A K, Keravnou E T, Pozzi G. Temporal representation and reasoning in medicine: Research directions and challenges. Artif Intell Med. 2006; 38(2):101-13; Post A R, Harrison J H. Temporal data mining. Clin Lab Med. 2008; 28(1):83-100; McGregor C. System, method and computer program for multi-dimensional temporal data mining. 2010. Patent 4 089705-0009; Canada, Gatineau Quebec; and McGregor C, Sow D, James A, Blount M, Ebling M, Eklund J, et al. Collaborative research on an intensive care decision support system utilizing physiological data streams. AMIA Annu Symp Proc; 2009:1124-6.

As is shown in the prior art, to date known methods that analyze data in this field of art have been highly based in statistics. Therefore, analyzing cross correlations of temporal behaviours is too computationally complex to be incorporated with prior art methods. Additionally, there has also been extensive focus on just the heart rate behaviour to the exclusion of other factors. For example, prior art real-time monitoring of physiological data shows a focus on the detection of the heart beat (known as the QRS complex) within the electrocardiogram (ECG) and analyzing the distance between two same parts (R) of the beating heart process. That distance is known as the R-R interval. The behaviour that may be determined from such methods is a reduced variance over time in the distance from one beat to the next over a sequential collection of R-R intervals.

Moreover, prior art methods function to utilize offline data that has been collected previously by way of computationally intensive techniques such as sample entropy, frequency histograms for a given time interval or standard deviations. Applying such maths to assess the state of variability is overly complex and is often not translatable to a computational method that can be run in real-time. For example, known sample entropy methods rely on looking at a significant number of intervals from the immediate past, and then using that to try and probabilistically see if it can guess the values in the future and the more accurate that ability to predict then the higher the score. This method therefore requires the availability of information from the future to see if the prediction was correct. Such a method cannot be run in real-time to provide useful results, as it requires operation of delay of several minutes. The result is that what just happened in the immediate past is essentially recognized as the future in such methods.

Moreover, standard deviation of the values of HR does not provide information regarding the distances from one HR to the next, but rather provides information about the spread of the values overall. The results do not provide details of variability because the HRs occur as a sequential stream that sequential information is integrated into the analysis.

SUMMARY OF THE INVENTION

In one aspect, the present disclosure relates to a system for identifying potential condition onset in one or more patients characterized in that it comprises: one or more medical monitoring devices operable to acquire heart rate and respiratory rate signals at regular intervals relating to one or more patients; a data analysis means operable to analyze the heart rate signals and respiratory rate signals to generate heart rate variability and respiratory rate variability values and to apply temporal abstraction analysis to said values to generate analysis data.

Said system of being characterized in that it further comprises the data analysis means being operable to utilize the values and analysis data to identify potential condition onset in patients.

Said system being characterized in that it further comprises the signals being acquired in real-time.

Said system being characterized in that it further comprises a clinical decision making support means.

Said system being characterized in that it further comprises the temporal abstraction analysis being operable to distinguish temporal patterns in the values.

Said system being characterized in that it further comprises the one or more medical monitoring devices including one or more of the following: a ECG monitor, or a drug infusion device.

Said system being characterized in that it further comprises a network operable to receive and transfer analysis data to and from the one or more medical monitoring devices.

Said system being characterized in that it further comprises a web service being operable to receive and transfer analysis data between the one or more monitoring devices and the network.

Said system being characterized in that further comprises a cloud based environment.

In another aspect, the present disclosure relates to a method for identifying potential condition onset in one or more patients characterized in that it comprises the following steps: acquiring heart rate and respiratory rate signals at regular intervals relating to one or more patients from one or more medical monitoring devices; analyzing the heart rate signals and respiratory rate signals to generate heart rate variability and respiratory rate variability values; applying temporal abstraction analysis to said values to produce TA data; and determining the potential condition onset relating to a patient based on the TA data.

Said method being characterized in that it incorporates the further step of, identifying trends that are temporal patterns in the TA data, said patterns being characteristic of potential condition onset.

Said method being characterized in that it comprises the further step of undertaking analyses of TA data to generate indicators of potential condition onset in patients.

Said method being characterized in that it comprises the further step of providing data relating to clinical conditions.

Said method being characterized in that it comprises the further step of providing narcotics data relating to any one of the following as data relating to clinical conditions and utilizing such data in the analysis: narcotics provided to one of the one or more patients; or surgery undergone by one of the one or more patients.

Said method being characterized in that it comprises the further step of plotting a score of variability relating to the values at regular intervals.

Said method being characterized in that it comprises the further step of setting temporal rules that are utilized in the determination of the potential condition onset relating to the patient based on the TA data.

Said method being characterized in that it comprises the further step of creating a classification scheme to the TA data.

Said method being characterized in that it comprises the further step of generating data relating to one of the one or more patients, and generating data relating to the one or more patients collectively.

In yet another aspect, the present disclosure relates to a non-transitory computer readable medium for identifying potential condition onset in one or more patients, characterized in that it comprises: a computer readable medium bearing software instructions; and the software instructions for enabling the computer to perform predetermined operations, the predetermined operations including the steps of: acquiring heart rate and respiratory rate signals at regular intervals relating to one or more patients from one or more medical monitoring devices; analyzing the heart rate signals and respiratory rate signals to generate heart rate variability and respiratory rate variability values; and applying temporal abstraction analysis to said values to produce TA data.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein.

Figure 1:
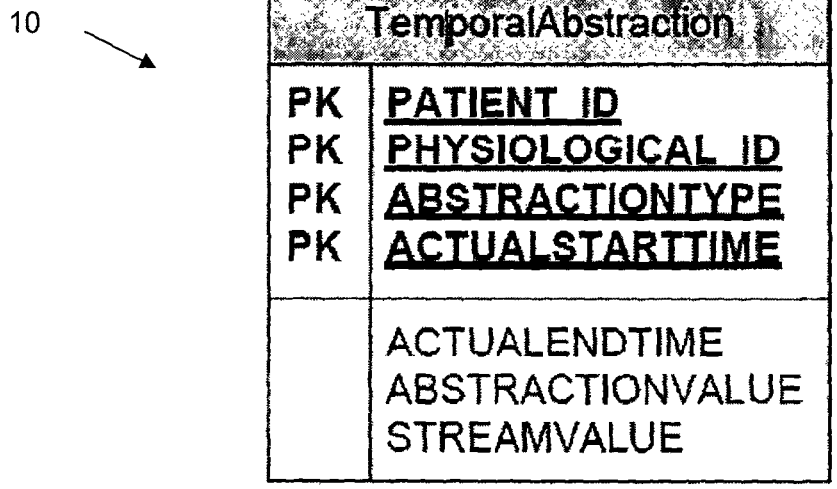
FIG. 1 is a schematic diagram of a temporal abstraction table in accordance with an embodiment.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

The present invention is a method and system for identifying potential condition onset based upon a combination of Heart Rate Variability (HRV), Respiratory Rate Variability (RRV) and/or confounding factors. The present method and system may involve data collection, a temporal abstraction (TA) based approach, and data analysis to identify potential condition onset in patients. The present method and system may generate and amend a classification scheme to be operable to determine that a patient is facing potential condition onset. The present method and system may further be operable to provide clinical decision making support. Embodiments of the present method and system may be operable to identify trends, such as temporal patterns, and to undertake a variety of analyses of collected and/or TA data to provide indicators, and determinations of potential condition onset in patients. As an example, the present method and system may be applied to identify potential condition onset of sepsis in infant patients.

The present invention may be a temporal abstraction (TA)-based method and system for distinguishing temporal patterns in time series data using HRV and Respiratory Rate Variability (RRV) and be operable to perform HRV analysis. Embodiments of the present invention may be operable to: cause HRV to be used for early identification of LONS using lower granularity 30 second spot readings; permit RRV to add value to HRV analysis by distinguishing between patients with low HRV due to imminent sepsis and those patients with low HRV due to the presence of confounding factors such as surgery, narcotics, and other drugs; and analyze the relationship between HRV and RRV to identify patterns in patient data associated with clinical situations. For example, the present invention may be operable to identify patients that should be monitored closely as they are exhibiting temporal patterns characteristic of the early, pre-clinical phase of a condition, for example, such as sepsis.

The present invention may incorporate data sources, and such data sources may be a database, or may be one or more machines or monitors, such as an ECG, a drug infusion, or other monitors or machines. The information may be provided to a computer that is operable to perform calculations and analysis based on the data provided to the computer. The calculations and analysis that embodiment of the present invention may provide are described herein. The present invention may further incorporate an input and/or output device whereby a user may input information or commands into the system, such as threshold settings, or a user may view or otherwise receive the output of the system, such as a display means. The present invention may further incorporate a reporting means, whereby one or more forms of reports may be generated.

The present method and system may further involve consideration of the effect of confounding factors. The present method and system may generally involve a TA-based approach for distinguishing temporal patterns in time series data using HRV and RRV and may include a means of utilizing and applying such temporal patterns. The present method and system may be operable to identify patients that should be monitored due to the fact that such patients are exhibiting patterns characteristic of potential condition onset, for example, such as temporal patterns characteristic of potential condition onset. The present method and system may involve data collection; a TA approach and analysis to define or amend a classification scheme and/or to provide clinical decision making support. Such classification scheme and/or clinical decision making support may be based upon a determination of patients that have heart rate (HR), respiratory rate (RR) and/or confounding factors that indicate the likelihood that the patent will be affected by the potential condition onset. The present method and system may be operable to provide real-time, virtually real-time functions.

The data collection of the present method and system may involve gathering data relating to HR and RR at regular intervals, for example, such as at intervals of 30 seconds. The data collection may further gather data relating to confounding factors, for example, such as surgery, narcotic administration, or the administration of other drugs. The present method and system may apply a TA approach to the collected data. Said TA approach may extract relevant features and identify states, trends and temporal relationships. The TA approach may further determine HRV and RRV patterns relating to individual patients. Analysis of the output of the TA approach may involve a variety of analysis methods and outputs, for example, such as one or more classification schemes, clinical decision making support, determination of "normal" or "baseline" values, and determining a role of confounding factors. A skilled reader will recognize that other analysis and outputs may also be possible.

As an example, the potential condition onset that may be identified by the present method and system may be sepsis. In such an example, the present method and system may identify patterns, such as temporal patterns, that are characteristic of sepsis. Some embodiments of the present method and system even may be operable to identify a potential condition onset, for example, such as sepsis. A skilled reader will recognize that this is but one example of an application of the present method and system to a potential condition onset and that other applications of the present method and system to other potential condition onsets are possible.

As another example, the present invention may be operable to observe the recovery of a patient after surgery. Some embodiments of the present method may be operable to recognize the patient response and recovery from the withdrawal of anaesthetic drugs post surgery.

As yet another example, the present invention may be operable to observe the response of a patient to muscle relaxation as a therapeutic procedure. Some embodiments of the present invention may be operable to determine the degree of muscle relaxation achieved based on the dosage of muscle relaxation.

The present invention provides certain benefits over the prior art, such as that in the majority of NICUs, current prior art information management practices do not make provision for storage and analysis of real-time data streams, with manual recordings every 30-60 minutes being the norm. The present invention overcomes this limitation of the prior art by providing for storage and analysis of real-time data streams.

The present invention provide another benefit over the prior art in that the prior art focuses upon the relationship between HRV and specific clinical conditions, whereas the present invention involves the relationship between HRV and RRV.

The present invention provides yet another benefit over the prior art in that it is a simpler, business intelligence-based approach to variability analysis, as compared to following a more conventional approach of the prior art that uses techniques such as sample entropy and approximate entropy. The present invention is computationally simpler to perform than sample entropy, as the present invention does not require any time at the start to work to use data for initial training. A prior art entropy approach requires a sample, for example it has to collect approx 10,000 heart rate readings, in order to train on the behaviour before it can start to assess whether it can predict the future. The present invention is operable to start assessing the variability distances from an early point of function, for example, such as after the first two readings.

The present invention is operable to leverage business intelligence to summarize the most recent clinical information as performance metrics to identify temporal patterns indicative of the onset of clinical conditions and may provide a flexible platform for the real-time analysis of time series physiological data streams. The present invention is further operable as a cloud based implementation where, for example, physiological signals such as HR and Respiration Rate (RR) are sent at regular intervals, for example, such as every 30 seconds, from a remote location, to monitor for potential condition onset at the central hub. In this manner the present invention is an application that may be particularly relevant when supporting health services delivery in resource-poor areas where millions of newborns die from sepsis each year.

The present invention offers still another benefit over the prior art in that it may be simpler approach to HRV analysis than the prior art, and thereby may enable the translation of research-level systems into clinical practice, while still providing high quality evidence-based support, and that such an approach could play an important complementary role with current HRV risk scoring systems.

The present invention provides another benefit over the prior art in that the prior art HRV analysis does not address the impact of narcotics and other drugs on early identification of conditions, for example, such as sepsis. The present invention is operable to address the impact of narcotics and other drugs on early identification of conditions, for example, such as sepsis.

The present invention is operable to measure the degree of variability in a manner that permits for a look back from the current time and an easy calculation of the variability that has occurred over a period of time, for example, such as the last hour, or the last 15 minutes, that may be called a window of time. To achieve this outcome the present invention involves each pair of distances in the sequence occurring in the window of time, and calculates and analyzes whether the absolute distance from one to the next is either, too similar, or very different, based on a set threshold. In particular the present invention does not necessarily assess the distance between heart beats, but instead assesses the difference in the HR values. If the HR values vary beyond a set threshold (so that the variance is more than the threshold) from one HR to the next the result is a classification as a variable. However, if the HR values do not vary beyond a set threshold, are equal to or vary less than the threshold, the result is a classification as not a variable. The total number of results classified as variable, or as not a variable, or both results, may be calculated.

The present invention does not require a reference back to the raw ECG signal that generates data at 1000 readings a second. Instead the present invention may reference a much slower rate stream. This slower frequency monitoring may be utilized in particular for remote monitoring, for example, such as may occur in remote communities or for ambulatory patients.

The present invention may apply an analytics approach to physiological data analysis. The present invention may further utilize the analytics approach and/or results therefrom to determine a measure. For example, the analytics approach may be applied to HR data to provide a measure for HRV. As another example, the analytics approach may be applied to RR data to provide a measure for RRV. Moreover the data and/or measures may be compared, for example, the HRV value may be compared to the RRV to see if the RRV value presents a clinically relevant measure on its own or whether a more useful measure is presented when RRV is used with HRV.

Thresholds applied by the present invention may vary. For example, the threshold for children will differ from that for adults because the heart rate average is slower for children and slower again for adults. The thresholds for premature infants will vary based on their corrected gestational age from those of children and adults. A skilled reader will recognize that a threshold to be set to enable correct classification in accordance with the method and system of the present invention may vary, and may be an absolute distance threshold set based on data at a 30 second spot reading, or may be another threshold.

The method and system of this present invention may be applied to various physiological data, for example, such as HR, RR, and measure values pertaining to the various types of data may be produced by the present invention.

The present invention may provide a variety of results. For example, the present invention may provide multiple class measures of value based on physiological data. In one embodiment of the present invention three classes of HRV may be determined, including normal range, elevated, and almost non existent variability. Prior art techniques report the variability over a sliding scale, but the present invention is operable to determine distinct classes. The present invention may undertake analysis to correlate measure values, such as RRV behaviour with HRV, to establish the reason for multiple classes.

The present invention may also provide analysis related to a combination of surgery, narcotics and a condition. For example, variability, or lack thereof, in measure of values generated by the present invention may be indicative of behaviours or other causes. Thus, a patient who is put on a ventilator and given a muscle relaxant so that the patient's breathing may be completely ventilator controlled rather than ventilator assisted may indicate with a particular variability of respiration. The present invention may incorporate multiple physiological data indicators and values, and therefore it may further be possible to identify that such a patient may further experience a loss of all variability in HR and a complete loss in HRV. Such indicators can assist with patient treatment as well as the recognition of indicators of any condition onset that may be affecting a patient.

The present invention may further provide analysis that may indicate particular effects of taking certain drugs upon physiological behaviours of a patient or measure values. For example, the present invention can indicate that certain drugs may cause reduced RRV. The trajectory of the recovery of RRV may further be tracked once a patient is no longer taking the drugs. In this manner the present invention may be utilized as a clinical support tool in the management of drug delivery.

Additionally, analysis of the present invention may indicate the patients on certain drugs that impact the variability analysis for the development of infection. This is significant as certain drugs may mask the ability for reduced measured values, such as reduced HRV, to be an indicator of infection for those patients based on prior art, as prior art only relates reduced HRV with infection. The present invention may detect increased variability as an indicator of infection for patients whose variability has been reduced as a result of the presence of the drugs. The present invention may analyze the data pertaining to such patients, including other physiological data, and generate measure valued, and use the measured values to identify indicators that may be utilized to determine if the patient is at risk for the onset of conditions. The use of multiple physiological indicators and the analysis of the present invention may cause the present invention to be capable of classifying measured values in a way that the prior art is unable to achieve. The ability to generate such classifications may permit the present invention to provide results that are not attainable by the prior art. Such results may be utilized to determine whether indicators of an onset of a condition exist, or if other factors are masking or creating results that appear to suggest onset of a condition, but are not true indicators of such an onset.

Embodiments of the present invention may incorporate drug data, such drug infusion data. Some prior art methods detect the presence of drugs in a patient's system by utilizing drug infusion pump data and correlating this with the HRV to provide further detail on what the HRV may mean. Other prior art may look up the drug data in the hourly chart. However, this is a coarse recording of drug data to give an accurate detailed description of how a patient's body may be recalculating. Drug infusion data in isolation only provides information regarding what is infused into a patient's body, not how the body is reacting to the drug infusion (i.e., the pharmacodynamic/pharmacokinetic behaviour). The present invention may integrate physiological data to determine multiple values (such as HRV and RRV) and may further incorporate drug data, such as drug infusion data. All of this data may be analyzed by the present invention, so that significant results including classification of body behaviours may be produced to indicate the effects of drugs and other physiological attributes and the likelihood of the combination of these to produce a condition onset in a patient.

The present invention may determine HRV and RRV from HR and RR respectively, and HR and RR may be calculated from ECG leads, such as the same three lead ECG leads. Therefore, the present invention represents a minimal requirement approach for data collection to be able to generate significant classifications of body behaviours.

The present invention may plot a score of variability at regular intervals, for example, such as hourly or every 15 minutes. Adjusting the intervals may be achieved by a user of the system. The interval may be set to achieve improved classification of when a change in physiological behaviour actually begins for a patient.

One embodiment of the present method and system may be applied as a non-invasive diagnostic tool. For example, such as an embodiment of the present method and system that may be applied to diagnose clinically important conditions of a patient that is a newborn infant.

Another embodiment of the present method and system may incorporate an interface design operable to support clinical decision making as business intelligence output. Such an embodiment of the present method and system may be operable to indicate patients that are exhibiting patterns characteristic of a potential condition onset. This indication may alert health workers that the patient should 'be monitored, and in some cases closely monitored, for the onset of the potential condition.

The present method and system may be operable to identify a high level classification scheme based on temporal behaviours for, and relationships between, HRV and RRV. Such a classification scheme may further be utilized to indicate "normal" or "baseline" values for patients in relation to HR, RR and/or confounding factors. Generally, the classification scheme may be utilized to identify patients within a particular classification, including patients that are outside the range of "normal" or 'baseline" HRV, RRV and/or confounding factor results. The present method and system may further be utilized to amend and update classification schemes subsequent to the creation of the classification schemes, such as for example, on-the-fly, at regular intervals, or upon an ongoing basis.

In another embodiment, the present method and system may be a cloud based implementation whereby HR and RR signals are sent at regular intervals from a remote location to a hub. The HR and RR signals may be sent for example, at intervals such as every 30 seconds. These signals may be utilized by the present method and system to monitor for potential condition onset, for example, such as the onset of sepsis. If potential condition onset is identified this information may be provided to the remote location. Such identification of potential condition onset and provision or related information to the remote location may occur in real-time or virtually real-time. The method and system may thereby support health service delivery in resource-poor areas where millions of newborns die from sepsis each year.

The present method and system may offer several benefits over the prior art. The prior art is frequently complex data processing algorithms provided as a black box to end users. The present method and system offers a benefit over the prior art in that the present method and system may allow for HRV to be used for early identification of potential condition onset, for example, such as late-onset neonatal sepsis (LONS). (LONS for the purpose of this method and system may refer to sepsis acquired on or after the fifth day of life, using lower granularity 30 second spot readings.) Additionally, the present method and system may utilize RRV which may add value to HRV analysis by distinguishing between patients with low HRV due to imminent sepsis and those patients with low HRV due to the presence of confounding factors such as surgery, narcotics, and other drugs. Still another benefit of the present method and system over the prior art may be that the present method and system may involve analysis of the relationship between HRV and RRV that may lead to identifiable patterns in patient data associated with clinical situations.

The present method and system may provide other benefit over the prior art as well. Prior art generally includes algorithmic approaches for the early identification of potential condition onset that involve data processing of algorithms that are inherently complex, often appearing as a black box to end-users. The present method and system may offer a simpler, business intelligence-based approach to variability analysis.

A further benefit of the present method and system over the prior art may be the data mining utilizations and operabilities of the present method and system. As described herein the present method and system may collect data that is not collected by the prior art, for example, such as confounding factors data. The present method and system may also apply a TA-based approach to such data that is not applied by the prior art. Moreover, the present method and system may undertake analyses and provide certain results that the prior art is not operable to undertake or provide, for example, such as clinical decision making support that incorporates considerations based on HRV, RRV and confounding factors. For these reasons, the present method and system may provide gather, create and store data that is not generated by, accessible by, or stored by the prior art, and consequently the present method and system may offer data mining functions and opportunities that are not possible for the prior art to include.

The present method and system may provide another benefit over the prior art in that infants in neonatal intensive care units ("NICU") frequently receive medications that affect the nervous system. However, prior art HRV analysis does not discuss the impact of narcotics and other drugs on early identification of potential condition onset. The present method and system may offer analysis of HRV that considers the presence of confounding factors that include narcotics and other drugs.

A skilled reader will recognize that several embodiments of the present method and system may be possible. The following provides one such embodiment of the method and system of the present invention, and this is presented merely as an example of one possible embodiment of the present method and system, other embodiments are also possible.

One embodiment of the present method and system may involve data collection, a temporal abstraction approach for determining variability, and an analysis stage.

The present invention may provide a TA-based approach for distinguishing temporal patterns in time series data using HRV and RRV may provide a system and method that address new research questions in the area of HRV analysis.

An embodiment of the present invention may be operable to store the raw data from multiple infants in real-time or virtually real time, at the rate that the data is generated. The present invention may further be operable to support data collected from multiple physical monitoring devices as well as from CIMS.

Figure 8:
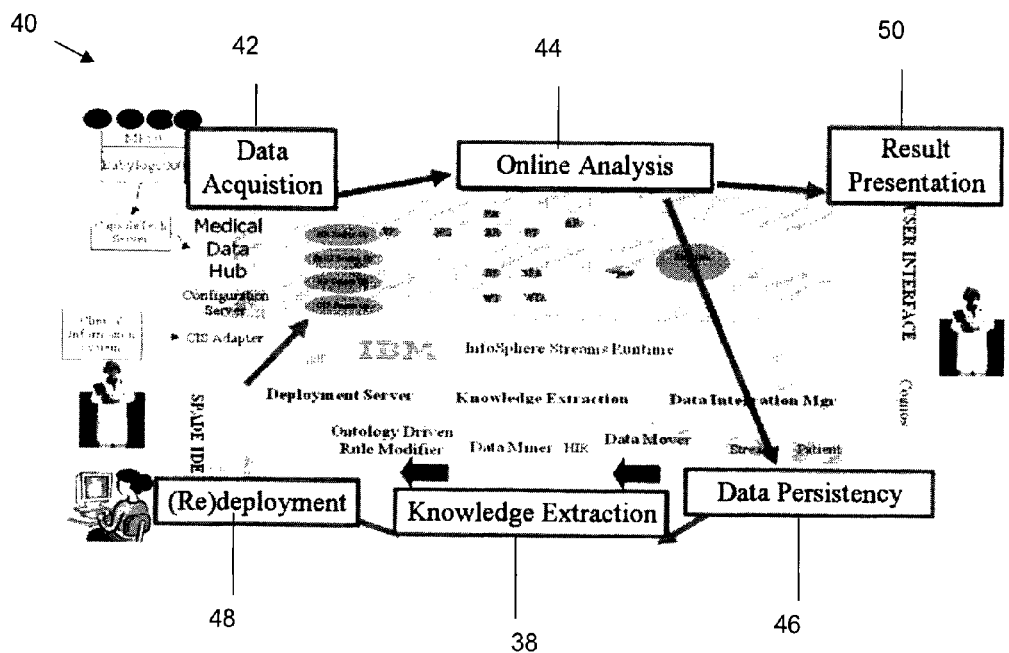
FIG. 8 is a schematic diagram of a representative framework for various embodiments.
Figure 9:
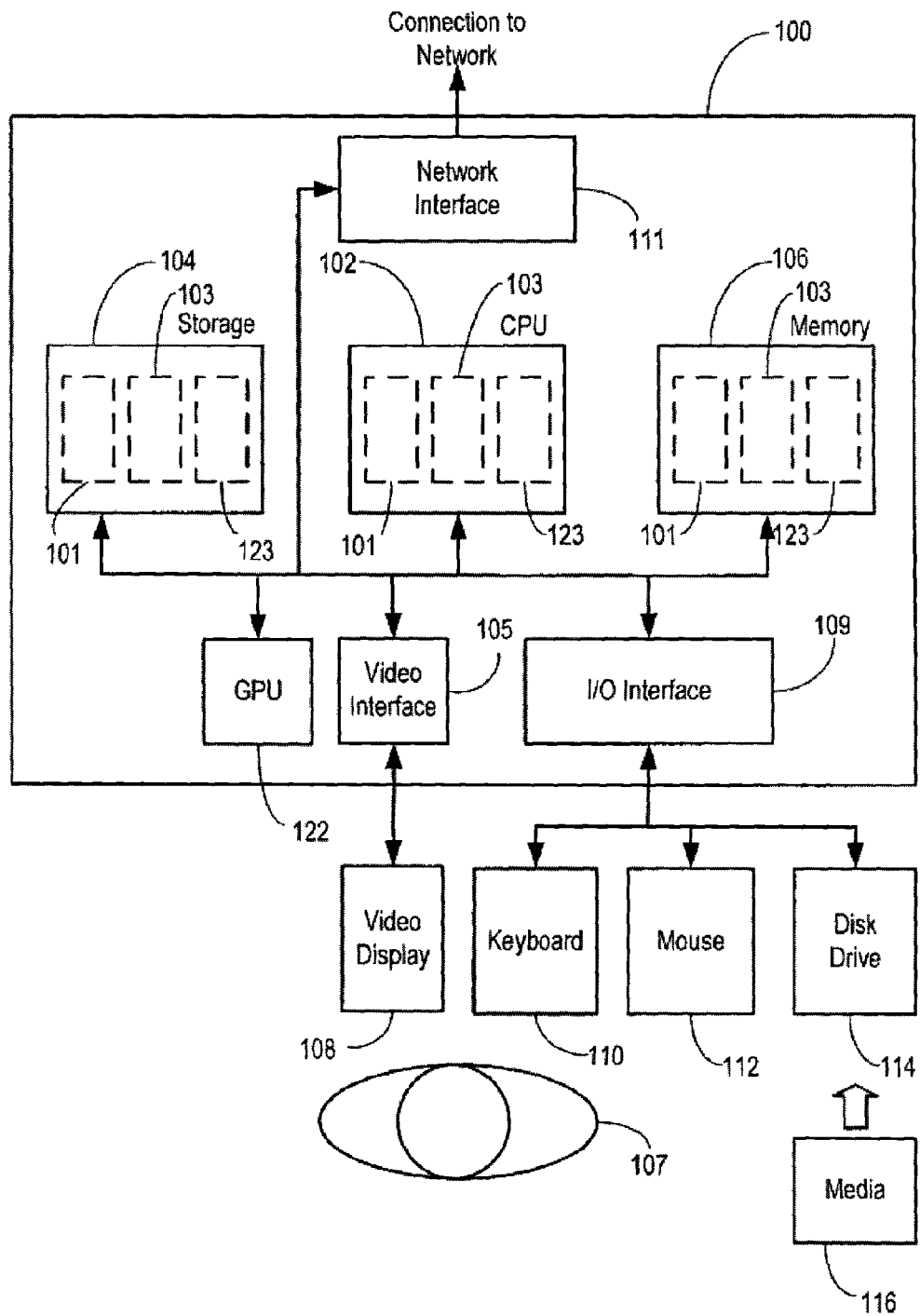
FIG. 9 illustrates a generic computing device and connected network which may provide an operative environment for various embodiments.

As shown in FIG. 8, one embodiment of the present invention may support the ingestion and storage of multiple real-time data streams from multiple patients, while analyzing for multiple conditions for the purposes of real-time and retrospective analysis, and data mining. The present invention may be operable to support clinical research within a knowledge extraction layer 38. An embodiment of the present invention that incorporates a system 40, such as that shown in FIG. 8, may be operable to create new rules, and to be implemented in real-time as part of the online analysis component. A skilled reader will recognize that the programming language of embodiments of the present invention may differ, for example, the present invention may use the Infosphere streams programming language: SPADE.

The present invention may be incorporated into a known system, such as an Artemis system, or other known systems. For example, the HRV and RRV analysis and calculations of the present invention may be implemented within medical devices, such as an MP50 medical monitoring device. For example, the method of the present invention may be incorporated in the software of medical monitoring devices.

Figure 10:
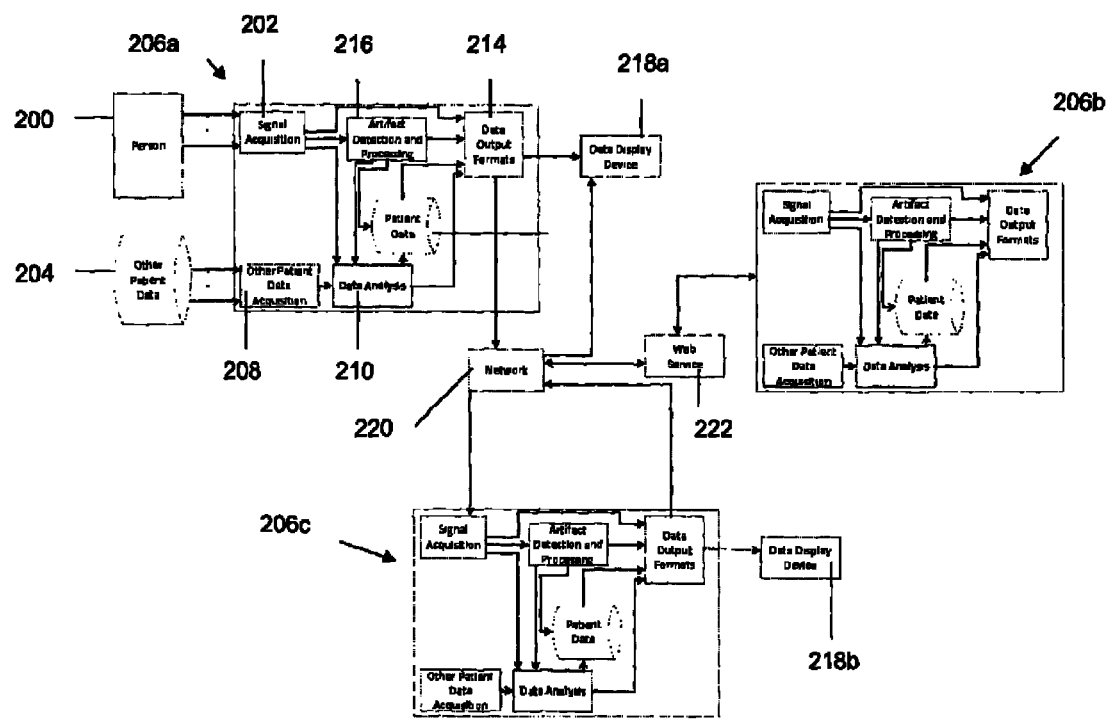
FIG. 10 illustrates an embodiment of the present invention incorporating a web service.

In one embodiment, as shown in FIG. 10, the system of the present invention may be incorporate a computing processor or processors operable by a computing system, such as a patient medical monitoring device 206a. The device may be connected, through wires or wirelessly, to sensors 202 operable to acquire one or more signals from a patient 200. The device may include a computer system that may operate one or more computing processors whereby one or more external physiological patient data streams from one or more patient data storage means 204 may be received by the device. The device may incorporate any or all of the following: one or more computing processors to receive one to many physiological patient data streams 208; zero or more computing processors to receive zero to many other pieces of patient information; such as that found in an electronic health record or laboratory information system; zero or more computer processors to compute artefact calculations and algorithms 216 being operable to remove or encode artefact found within the physiological data stream; and/or one to many computer processor to perform manipulations and calculations on the physiological data 210 such as the analysis and calculations of the present invention. The system may further incorporate one or more computer modules operable to display one or more forms of information from the physiological data streams.

Such a device may further comprise a computer processor to output the results and/or reports 214 of the present invention. The results may be displayed to a user on a data display device 218. The computing processor may further incorporate one or more of the following: a database output operator operable to enable the row insertion within a database; an output operator to generate emails or other notifications, an output to a computer processor accessing the outputted data locally or over a network 220; and/or an output of the data for insertion within the database of an electronic health record database 212, that may be a database of an external system. A skilled reader will recognize that other analysis and outputs may also be incorporated in the present invention.

In an embodiment of the present invention, the system may include a computing processor or processors within a computing system such as a patient medical monitoring device operable to acquire physiological data either through direct connection or via a connection over a network form another computing device that performs the function of the connection to the sensors acquiring the signal from the patient, and zero or more computer processes to compute artifact calculations and/or algorithms to remove or encode artefact found within the physiological data stream. Such an embodiment of the present invention may contain any of the following: one or more computing processes operable to receive the one or more physiological data stream; or zero or more computing processes to receive zero or more other pieces of patient information such as that incorporated in an electronic health record or laboratory information system; one or more computing processes operable to perform manipulations and calculations based on the physiological data in accordance with the present invention; and/or one or more computer modules to display one or more forms of information from the physiological data streams. A skilled reader will recognize that other analysis and outputs may be generated by the present invention.

The present invention may further incorporate multiple patient medical monitoring devices 206a, 206b, 206c, as shown in FIG. 10. The devices may be connected to a network 220 so that: the devices provide output data to the network directly; the network can receive and send data back-and-forth to and from a device; and/or the device transfers data back-and-forth between a network and the device via an additional component, for example, such as a web server 222. In this embodiment of the present invention multiple sources of data from multiple monitoring devices, patient data record sources, and/or multiple patients may be incorporated in the present invention. The output of the present invention may further be displayed on multiple data display devices 218a, 218b, so that data that is combined data, or data that is specific to one device may be displayed to a user.

Embodiments of the present invention may incorporate known data streams, for example, such as IBM Infosphere Streams. Data may be manipulated as a stream as the data arrives in real-time or virtually real-time. The present invention may be operable as a stream computing program that receives the data streams directly from patient monitoring sensors as the data arrives in real-time or virtually real-time. Other pieces of information available on an electronic health record or laboratory information system may also be provided to the present invention. Output TAs may be calculated by the present invention through one or more of the following: a database output operator operable to enable the row insertion within a database; an output operator to generate emails or other notifications; an output to a computer process accessing the outputted data locally or over a network; and/or an output of data for insertion within a database of an electronic health record software program's database. A skilled reader will recognize that other computing output components may also be incorporated in the present invention.

An embodiment of the present invention may be a system that is operable with one or more known database engines or similar technologies. The invention may comprise a computer system that includes one or more computers that incorporate at least a temporal utility. The computer system may be linked to one or more database engines or similar technologies. The database engines may include one or more of the following: static data; and/or data from one or more remote devices or sensors. The computer system may be linked to one or more remote medical monitoring devices or sensors, through a wired or wireless connection that may be direct or indirect. The present invention may be operable to populate one or more database provided by the one or more database engines or similar technologies with sensor data. The function of the TAs may be represented within a TA rule table within a database.

In one embodiment of the present invention incorporated in a system, as shown in FIG. 8, the medical device may incorporate a computer and may be attached to a data hub 39 of a system, such as an Artemis system that is disclosed in Blount M., et al., "Real-Time Analysis for Intensive Care Development and Deployment of the Artemis Analytic System", IEEE Engineering in Medicine and Biology Magazine (March/April 2010), at 110-118; and McGregor C., et al., "Next Generation Neonatal Health Informatics with Artemis", User Centred Networked Health Care, Moen A., et al. (Eds.) (IOS Press, 2011) doi:10.3233/978-1-60750-806-9-115, at 115-119.

The Artemis system may be integrated with the present invention, as the Artemis system provides a flexible platform for real-time analysis of time series physiological data streams extracted from a range of monitors to detect clinically significant conditions that may adversely affect health outcomes. The data acquisition element 42 of the system may be operable to provide real-time synchronous medical device data and asynchronous clinical information management system data. The data may be forwarded to the online analysis element 44, operable in real-time, for analysis. The system may incorporate streaming middleware system operable to process data in real-time and compatible with the data persistency element 46 of the system to cause data to be stored by the system. The system may process and then store raw data as well as derived data from multiple infants at the rate that the data is generated. Stream processing may be supported by a programming language compatible with the streaming middleware system. The knowledge extraction element 38 may incorporate a temporal data mining means that supports the discovery of condition onset behaviours in physiological data streams and associated clinical use within the online analysis through a re-deployment element 48 operable to translate the knowledge to an output representation. Output of results of the analysis of the system may be provided to a user by way of the result presentation element 50. The output of results may be the in the form of reports that may be printed, displayed on a screen to a user, or provided as a notification to a device, for example, such as a smart phone or other device. The analysis and calculations of the present invention may be integrated in the analysis element of the Artemis system, or the knowledge extraction elements of the Artemis system, or in other elements of the Artemis system, in embodiments of the present invention. A skilled reader will recognize that the present invention may be integrated with other known systems.

Another embodiment of the present invention may incorporate a data hub that is linked to a data acquisition component. In other embodiments of the present invention the analysis and calculations of the present invention may be incorporated in a knowledge extraction component of a system. For example, the knowledge extraction element of an embodiment of the present invention may incorporate a DB2 database engine, and SQL statements may be utilized to construct the temporal abstractions as rows in the temporal abstraction table that can then be viewed by a user. Temporal abstractions may be implemented using a programming language incorporated in the system, such as SPADE or SQL. The online analysis element of the present invention may be compatible with such programming languages.

A skilled reader will recognize that the present invention may be implemented in known systems or novel systems in a variety of manners and may be incorporated in a variety of elements of such systems.

The present method and system may receive a data set, or may undertake data collection. In an embodiment of the present method and system that undertakes data collection, such collection may involve gathering data that is one or more of the following: (i) HR and RR sampled at regular intervals, for example, such as 30 second intervals; and (ii) confounding factor information from real-time data streams from multiple physical monitoring devices or databases, for example, such as multiple conditions, culture positive sepsis, surgery, administration of narcotics and other drugs. The data collection of the present method and system may involve a flexible platform for the real-time analysis of time series physiological data streams (e.g., multiple real-time data streams from multiple patients) to analyze multiple conditions and permit retrospective analysis and data mining.

The present method and system may incorporate a means to achieve a temporal abstraction approach for determining variability. Such an approach may involve several steps. The approach may involve transforming time stamped data into an interval-based representation of the data by extracting the most relevant features, for example, such as identifying states, trends and temporal relationships. The approach may further summarize sections of data that hold true for certain criteria and may identify a start time and end time over which the criteria is true. Additionally the approach may extract HR and RR streams. Such streams may be utilized to calculate variability. Variability calculations may involve taking the absolute value of the difference between two consecutive time points (for example, such as 30 seconds). HRV and RRV may further be determined based on calculating the number of minutes of low variability per hour, for the entire duration of the patient's NICU admission. The present method and system may also calculate other abstraction results, for example, such as hourly abstraction results. HRV and RRV patterns may be determined for each patient The present method and system may undertake several types of analysis and may achieve several different types of outputs, for example, such as classification schemes, clinical decision making support, determinations of "normal" or "baseline" values, determining the role of confounding factors, etc. A skilled reader will, recognize the wide scope of possible analysis that the present method and system may apply.

An embodiment of the present method and system may analyze the present method and system to identify, develop or refine a classification scheme. Such a classification scheme may be based on variability analysis. As an initial step the present method and system may identify periods of interest based on HRV and RRV results, for example, such as results for multiple patients, or a class of patients (e.g., patients at a particular institution, patients of a particular gestational stage, patients of a particular birth weight, etc.). This step may produce temporal patterns. These temporal patterns may be overlaid on clinical findings, and through the overlay it may be possible to identify, develop and/or refine a classification scheme based on variability analysis. Associations in trends in HRV and RRV and the clinical situations may be identified and these may be utilized to identify, develop and/or refine a classification scheme.

The present method and system may also be operable to provide clinical decision making support. Such support may be based on an analysis of the data of the present method and system that identifies patients that should be monitored because they are exhibiting temporal patterns characteristic of a potential condition onset, such as sepsis. Such support may also be based on an analysis of the data of the present method and system that identifies patients that are normalizing after surgery to determine when a patient may be moved on to subsequent treatment steps. Clinical decision making support may be provided to a health care working in a variety of manners and may be provided to health care workers that are remote from the location of elements of the present method and system, or any hub of the present method and system.

The present method and system may be operable to analyze data to determine "normal" or "baseline" Values. For example, the present method and system may determine normal or baseline values based on an analysis of the data that identifies gestational age and birth weight of patients to determine thresholds for HRV and/or RRV for different gestational age and birth weight combinations. The present method and system may also be operable to compare "normal" or "baseline" HRV and/or RRV values between two or more institutions.

The present method and system may be operable to determine the role of confounding factors in the potential condition onset. The present method and system may undertake an analysis of data to determine how much of the rise in low HRV and/or RRV is due to particular confounding factors, for example, such as surgery and particular narcotics or other drugs. The present method and system may also undertake an analysis of data to determine the effect of particular surgeries, narcotics or other drugs upon the potential condition onset. A skilled reader will recognize the other analysis of confounding factors that may be undertaken by the present method and system.

The present method and system may be operable to perform other types of analysis for other purposes and outputs as well, for example, such as analysis to differentiate palliative patients and cases. Such analysis may be involve other analysis methods and/or techniques of the present method and system, such as comparisons of data to normal or baseline values to determine palliative patients. Such analysis may also be utilized by the present method and system to provide other analysis outputs, such as clinical decision making support, whereby the health care workers are alerted to the palliative nature of a patient or a case. A skilled reader will recognize that analysis means and methods may be supplemented and combined in other manners to produce other analysis and outputs as well.

It will be appreciated by those skilled in the art that other variations of the embodiments described herein may also be practiced without departing from the scope of the method and system. Other modifications are therefore possible. For example, the present method and system may be utilized with data other than patient-related data. The present method and system may be applied to generate predictive trend analysis utilizing a variety of types of data other than patient data. In this manner the present method and system may be applicable to multiple streams of variable data. The present system and method may be practiced in various embodiments. A suitably configured computer device, and associated communications networks, devices, software and firmware may provide a platform for enabling one or more embodiments as described above. By way of example, FIG. 10 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 110, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown).

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present method and system. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

EXAMPLE

An example of an embodiment of the present invention is provided herein. A skilled reader will recognize that this is merely provided as an example of one application of the present invention and that other embodiments and applications of the present invention are possible.

This example embodiment of the present invention was operable in reference to an observational study that analyzed retrospective data obtained from admissions to the NICU at The Hospital for Sick Children, Toronto between Jun. 1, 2008 and Nov. 30, 2008, comprising a total of 218 patient cases. Patient data was analyzed for the full duration of the neonate's NICU admission. As the focus was on LONS, patients with less than five days of total data were excluded. Patients were included in the analysis regardless of gestational age at birth, birth weight, or presence of congenital abnormalities, co-morbidities or medications. Physiological parameters of interest included derived HR and RR, both sampled every 30 seconds. Clinical knowledge was obtained retrospectively from the NICU's Clinical Information Management System (CIMS); this included: culture positive sepsis, surgery, administration of narcotics and other drugs. The research was approved by the Hospital's Research Ethics Board.

The embodiment of the present invention in this example incorporated Temporal Abstraction (TA) applicable to deal with time series data in the medical domain. The first step of the method of the present invention may involve transforming time stamped data into an interval-based representation of the data by extracting the most relevant features, such as identifying states, trends and temporal relationships. Then sections of data that hold true for certain criteria can be summarized with a start time and end time over which this criteria is true.

After extracting both HR and RR streams, variability may be calculated by taking the absolute value of the difference between two consecutive time points, for example, such as every 30 seconds. In order to identify periods of low variability, the abstraction value for a time period is based on the total number of minutes in that period during which the absolute value is less than a given threshold, th—as shown in Equation 1. When th is raised, the number of minutes of low variability will decrease, as this corresponds to a looser criterion for variability. The optimal value for th was determined through experimentation for each physiological parameter, taking into account known normal variations in both HR and RR for neonates; resulting in th_HR=4 and th_RR=3. HRV and RRV were determined based on calculating the number of minutes of low variability per hour, for the entire duration of the patient's NICU admission.

As an example, in an embodiment of the present invention that obtains 30 second spot readings this results in two readings a minute and a total of 120 readings an hour; to calculate the total minutes of low variability per hour the final summation is divided by two. Hourly abstraction results are calculated using the percent of valid rows only for each hour. In the example embodiment of the present invention this accounted for instances where complete data was not collected in a given hour, or when complete hours were missing; for example, when a patient is in the operating room.

Temporal abstraction-based $HRV$ and $RRV$ for time series Equation 1

$$p(t) = p(|1 + p(2) \ldots p(\text{total hours})$$

$$\forall t \in p(t): HRV(t) = \left(\sum_{n=1}^{120} (|HR_n - HR_{n+1}| < \text{th\_HR})\right)/2$$

$$\forall t \in p(t): RRV(t) = \left(\sum_{n=1}^{120} (|RR_n - RR_{n+1}| < \text{th\_RR})\right)/2$$

The present invention may be operable to identify a high level classification scheme based on temporal behaviours for, and relationships between, HRV and RRV. In this example embodiment of the present invention, a Service-based Multidimensional Temporal Data Mining ($STDM''_O$) Framework was utilized. A skilled reader will recognize that other frameworks may be applied. As part of the framework applied, temporal abstractions were stored within the TemporalAbstraction table. Seven data elements for each patient were stored in the SQL TemporalAbstraction table 10, as shown in FIG. 1; PATIENT_ID links specific abstractions to specific patients; PHYSIOLOGICAL_ID relates the abstraction to a physiological value, such as HR or RR; ABSTRACTIONTYPE indicates the type of abstraction, such as a trend, level shift, or threshold breach; ABSTRACTIONVALUE holds the abstraction results; ACTUALSTARTTIME and ACTUALENDTIME indicate the time period over which the abstraction holds true; and STREAMVALUE represents stream specific information at that time.

Figure 2:
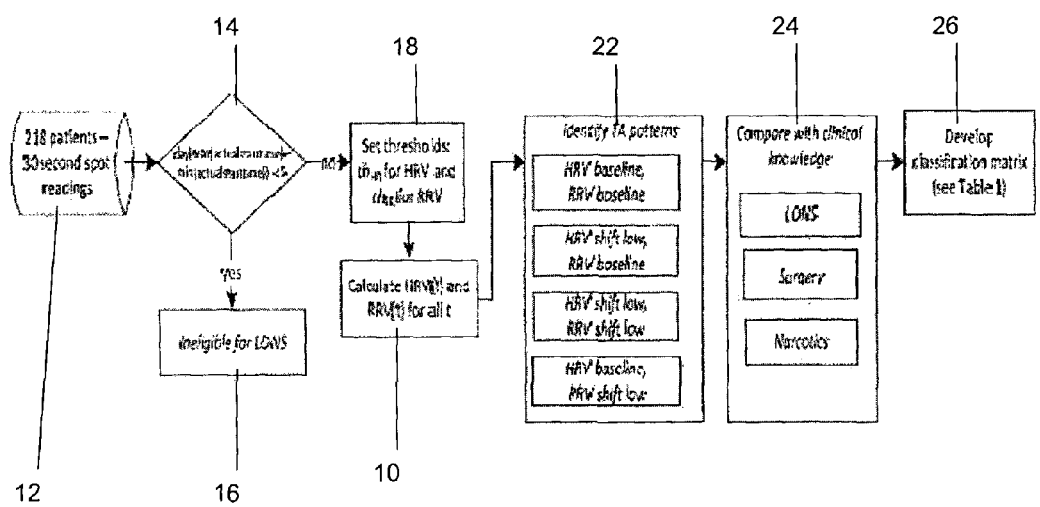
FIG. 2 is a study protocol in accordance with an embodiment.

The present invention may further analyze patient data using the following protocol, involving a system or method, as is shown in FIG. 2. The protocol may involve collecting patient data collected over a time intervals such as may be stored in a database or other data set 12. The patient data records may be analyzed 14 to determine the status of patients in relation to baseline thresholds. A patient may be deemed ineligible 16 so that the patient record will not be further analyzed by the protocol. Thresholds may be set 18 for the analysis of eligible patient data, and calculations 20 may be performed utilized the data. Patterns in the data, for example, such as TA patterns, may be identified in the data 22, and the patterns may indicate baselines or other details pertaining to the data. The results of the analysis of the data may be compared to clinical knowledge 24 to determine if the results are consistent with prior knowledge. The clinical knowledge may be divided into categories, for example, such as LONS, Surgery and Narcotics. A classification matrix may be developed 26.

In this example embodiment of the present invention, for selected patients, relevant clinical information, as detailed above, was extracted from CIMS and time periods of interest were identified for the diagnosis of proven LONS, surgery and narcotics. This task was performed by a clinical expert independently from the data analysis component of the research. Concurrently, the data analysis group applied TA techniques to determine HRV and RRV patterns for each patient. Subsequently, the data analysis team identified time periods of interest based on the HRV and RRV results. Finally, the clinical findings were overlaid on the temporal patterns to identify, develop and refine a classification scheme based on variability analysis.

A test of a first hypothesis that 30 second spot readings can be used to flag patients with periods of reduced HRV for early identification of LONS found that low HRV alone was inadequate for this task because HRV is also impacted by other clinical situations.

To reduce the false positives for LONS, the present invention may include information for RRV and examine the relationship between HRV and RRV, which is a means of identifying a predictive pattern for LONS. Through retrospective TA-based data analysis and discussion with clinical experts, it was determined that surgery and administration of narcotics and other drugs resulted in both reduced HRV and reduced RRV; with both values often reaching greater than 58 minutes of low variability per hour in the immediate postoperative period. Based upon this knowledge, the example embodiment of the present invention is operable to identify four patterns for HRV and RRV found to be associated with particular clinical situations. These situations include: 1) patients with proven LONS; 2) postoperative patients receiving narcotics and other drugs (e.g. morphine, codeine, muscle relaxants); 3) non post-operative patients receiving narcotics and other drugs; and 4) patients that are negative for these three classifications. The identified associations between trends in HRV and RRV and the clinical situations are presented in Table I's classification matrix, as shown below.

TABLE 1

|  | HRV Baseline | HRV Shift Low |
|---|---|---|
| RRV Baseline | Negative on classifications for LONS, surgery, and narcotics or other drugs | Patients with proven LONS (LONS+) |
| RRV Shift Low | Uncommon | Post-operative patients receiving narcotics or other drugs (SURGERY + NARCOTICS) Non post-operative patients receiving narcotics or other drugs (NARCOTICS) |

At different points in time during their NICU admission, a patient can be classified into different clinical situations, such as a post-operative patient that subsequently develops LONS. Representative examples are presented for each matrix category, with the exception of HRV Baseline—RRV Shift Low, which is a rare occurrence. For each patient example, abstractions from the entire length of the NICU stay are provided; however, to protect patient identity, all data is shown starting from the same date: Jan. 1, 2008 0:00.

Figure 3:
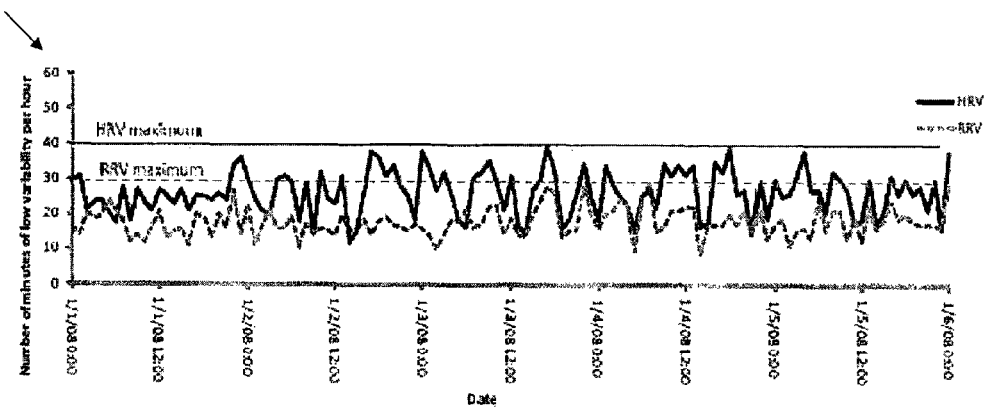
FIG. 3 is a representative HRV/RRV TA pattern for a NICU patient negative for LONS+, SURGERY+NARCOTICS, and NARCOTICS.

As is shown in FIG. 3, a representative table 28 provides an example of a HRV/RRV TA pattern for a patient negative for LONS, surgery, and administration of narcotics or other drugs. Although patients negative for these three classifications have different length of NICU admission, clinical diagnoses, and gestational age at birth, several generalities were identified amongst patients, as shown in FIG. 3: 1) HRV does not exceed 40 minutes of low variability per hour (average: 26.2, standard deviation: 6.4, min: 12, and max: 39); 2) RRV does not exceed 30 minutes of low variability per hour (average: 17.8, standard deviation: 4.2, min: 8, and max: 29); and 3) in general, the HRV and RRV patterns follow similar trajectories. These findings represent marked differences in TA HRV/RRV patterns as compared to those for patients classified under LONS+, SURGERY+NARCOTICS, or NARCOTICS.

Figure 4:
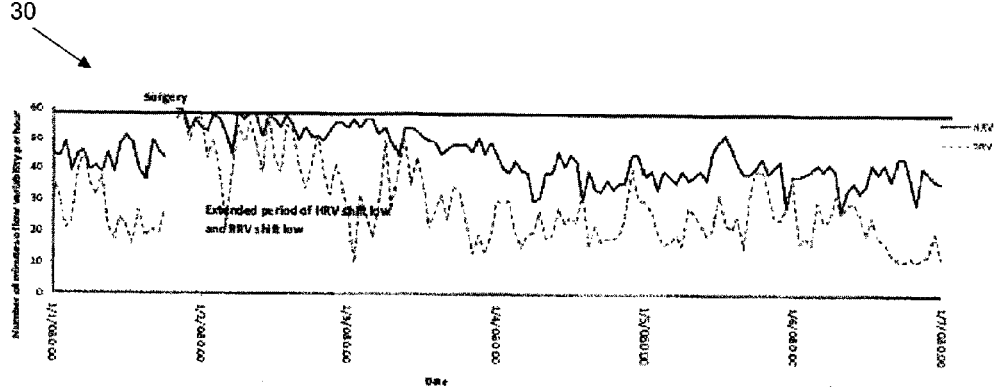
FIG. 4 is a representative HRV/RRV TA pattern for SURGERY+NARCOTICS.

As shown in FIG. 4, a representative table 30 for HRV/RRV TA shows patterns relating to a representative postoperative patient receiving narcotics. Leading up to the surgery event on Jan. 1, 2008 19:00, the number of minutes of low HRV and RRV per hour are as follows: HRV—average: 44.1, standard deviation: 4.3, min: 37, and max: 51.6; RRV—average: 37.5, standard deviation: 8.6, min: 16.3, and max: 45.6. During surgery, there is a one hour gap in data collection when the leads are removed; leads are re-connected postoperatively at 20:00. Postoperatively, the patient receives a narcotic infusion and antibiotics; at this point both HRV and RRV values spike to 60 minutes of low variability per hour. Gradually decreasing dosages of narcotics are continually administered from Jan. 1, 2008-Jan. 5, 2008; once narcotics and the impact of the drugs subside, and the infant stabilizes following surgery, both HRV and RRV return to pre-operative baseline levels.

Figure 5:
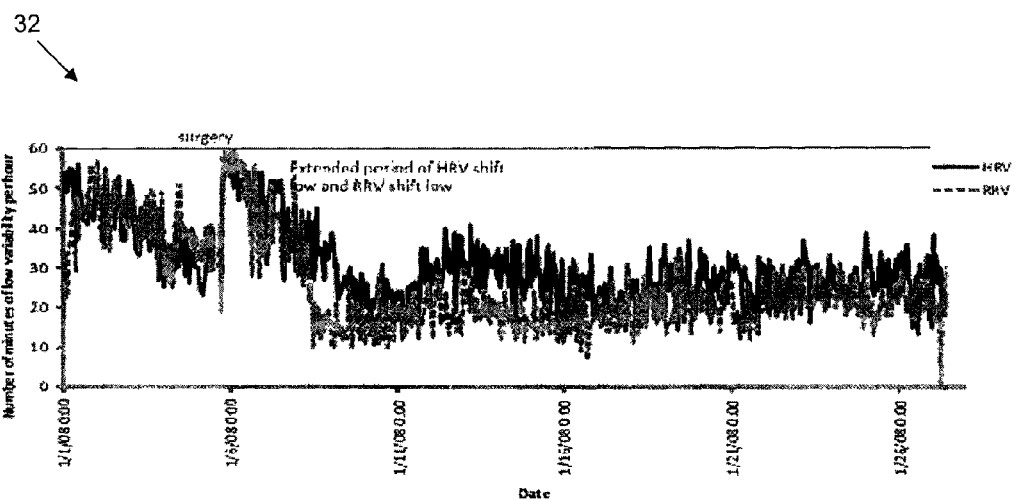
FIG. 5 is a representative HRV/RRV TA pattern for NARCOTICS followed by SURGERY+NARCOTICS.

As shown in FIG. 5, a representative table 32 for HRV/RRV TA shows patterns for an infant scheduled for major surgery Jan. 5, 2008 at 14:25. In preparation for the surgery, the infant received narcotic infusions starting Jan. 1, 2008. Post-operatively, when the leads are reconnected at 16:00, HRV spikes to 58 minutes of low variability per hour; RRV is lower still, reaching 60 minutes of low variability per hour. This patient is an example of a patient on narcotics, with low HRV/RRV, who then undergoes surgery and receives subsequent additional narcotics resulting in further reductions in HRV/RRV. In the days following surgery, HRV and RRV gradually increase as the infant stabilizes and the impact of the narcotics subsides. Throughout our retrospective analysis, we continually observed this pattern of extremely low HRV and RRV in the immediate post-operative period and upon administration of narcotics, which occurred frequently at time of NICU admission. In cases where the patient stabilizes, the HRV and RRV gradually return to pre-operative levels.

Figure 6:
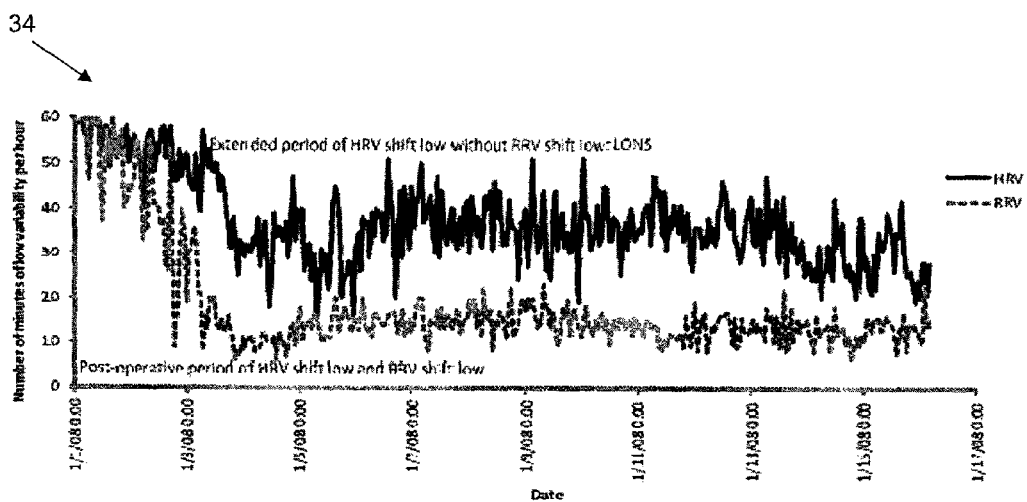
FIG. 6 is a representative HRV/RRV TA pattern for LONS.

As shown in FIG. 6, a representative table 34 for HRV and RRV TA show patterns for a LONS patient that developed IONS following surgery; this patient underwent surgery upon admission Jan. 1, 2008. During the immediate post-operative period (SURGERY+NARCOTICS), both RRV and HRV are extremely low: HRV spikes at 59 minutes low variability per hour and RRV reaches 60 minutes. By Jan. 3, 2008, as the impact of the narcotics subsides, both HRV and RRV have started to normalize. However, shortly after this time, the HRV has another low shift, and as of 01104/2008 0:00 the HRV continues to decrease. This patient is diagnosed with culture positive LONS on Jan. 5, 2008, almost two days after the RRV returned to normal levels and the HRV remained low, indicating that HRV/RRV TA patterns have potential value in the early identification of LONS. As compared with SURGERY+NARCOTICS and NARCOTICS patients, that exhibit extremely low HRV and RRV, we find that LONS cases are characterized by such extended periods of moderately low HRV without correspondingly low RRV. During the LONS period identified in FIG. 6 the HRV and RRV are as follows: HRV—average: 36, standard deviation: 6, min: 32, and max: 51; RRV—average: 11.5, standard deviation: 0.7, min: 11, and max: 23.

Figure 7:
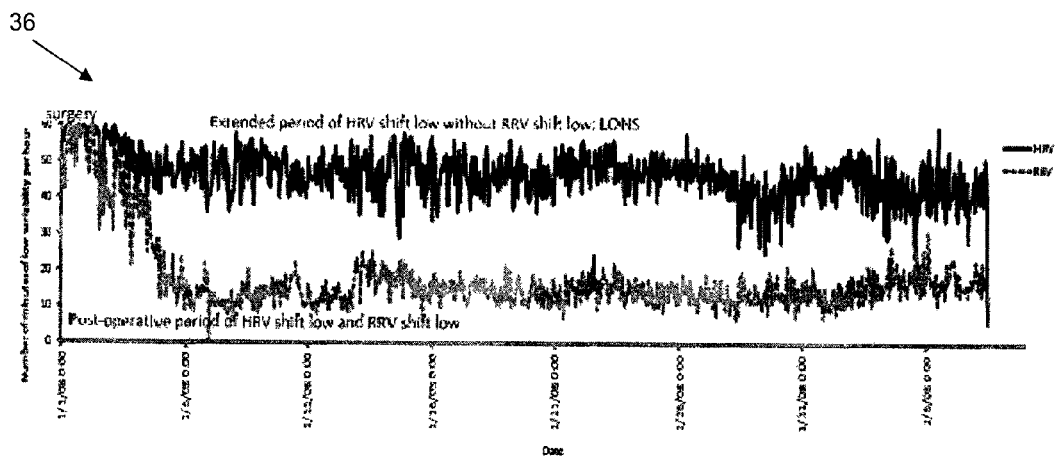
FIG. 7 is a second representative HRV/RRV TA pattern for LONS.

As shown in FIG. 7, a representative table 36 shows a further example of post-operative LONS. This patient underwent surgery Jan. 1, 2008 12:00. During this period the patient received narcotics and muscle relaxants (SURGERY+NARCOTICS) and RRV and HRV are extremely low, with both spiking at 60 minutes of low variability per hour. By Jan. 4, 2008, as the impact of the narcotics and muscle relaxants subsides, HRV and RRV begin to normalize—However, while the RRV continues to increase, HRV has another low shift. There is an extended period of low HRV without low RRV shown in FIG. 7, and this is similar to the pattern shown in FIG. 6. This patient is diagnosed with culture positive LONS on Jan. 11, 2008.

The operability of the present invention to assess variability across both HRV and RRV may reduce false positive rates in the real-time detection of LONS due to the classification of other factors that can cause reduced HRV, for example, such as surgery and administration of narcotics or other medications. The operability of the present invention to analyze variability may produce a clearer distinction between these other factors and LONS based on easily discernible varying threshold levels. The present invention may also provide a user interface design that can allow the output of the business intelligence to support clinical decision making.

Embodiments of the present invention may be operable in a cloud computing environment, such as an environment provided by an external service through a series of web services. The system couple also be implemented as a proprietary solution still accessible via the set of web services where data from one source, or from multiple sensors, is provided to a web server. The web server may be connected to the Internet and linked to at least the temporal utility of the present invention. The web server may deliver temporally abstracted data, or output of the analysis methods, calculations and outputs of the present invention. TA rules of the present invention may be incorporated in the system. Such TA rules may be added, modified or deleted by a user from a web service. The web service system of the present invention may offer a benefit over the prior art in that it may incorporate multiple organizations like to the web server and thereby provide a larger number of data sets to the present invention for analysis. Prior art systems generally receive a single data set. The incorporation of multiple data sets, and data sets from multiple organizations, has the benefit that it allows the present invention to provide improved data accessibility by each of the participating organizations.

It will be appreciated by those skilled in the art that other variations of the embodiments described herein may also be practiced without departing from the scope of the invention. Other modifications are therefore possible. For example, further enhancements to the disclosed system, method and computer program are envisioned, and without limiting the generality of the foregoing, the following specific enhancements are envisioned.

We claim:

1. An automated clinical decision support system configured for managing drug delivery to one or more patients based on generated predictions of potential late onset neonatal sepsis in the one or more patients estimated based on at least on computational analysis of encoded time series data obtained indicative of one or more relationships between heart rate variability (HRV) scores and respiratory rate variability (RRV) scores, the system comprising:

a) one or more medical monitoring devices operable to acquire time series drug infusion data indicative of one or more characteristics of drug infusion events, and time series heart rate and respiratory rate signals at regular intervals relating to one or more patients and to record the time series heart rate and respiratory signals as the encoded time series data; and b) a data analysis means operable to:

analyze the encoded time series data to generate the heart rate variability (HRV) scores and the respiratory rate variability (RRV) scores, the HRV and RRV scores obtained by relations:

$$\forall\, t \in p(t): HRV(t) = \left( \sum_{n=1}^{120} (|HR_n - HR_{n+1}| < \text{th\_HR}) \right) / 2$$

$$\forall\, t \in p(t): RRV(t) = \left( \sum_{n=1}^{120} (|RR_n - RR_{n+1}| < \text{th\_RR}) \right) / 2,$$

where HR is a heart rate for a given point in time, RR is the respiratory rate for the given point in time, th_HR is a heart rate threshold, and th_RR is a respiratory rate threshold, the HRV scores and RRV scores each indicative of corresponding numbers of periods of low variability;

apply temporal abstraction analysis to the HRV and the RRV scores to generate analysis data by distinguishing temporal patterns in the HRV and the RRV scores to identify periods of high variability and low variability correlated to the one or more characteristics of the drug infusion events to identify characteristics of physiological responses to the drug infusion events represented in the temporal patterns found in the HRV and RRV scores;

generate or update a classification matrix based on the distinguished temporal patterns, the classification matrix determined based on one or more identified relationships between the HRV and the RRV scores, the classification matrix maintained in relation to a target demographic population subset receiving similar drug infusion events;

store the classification matrix in a data structure on a data record associated with the one or more patients;

periodically apply the classification matrix to the HRV and RRV scores, obtained by said relations, of another specific patient to generate a prediction of potential late onset neonatal sepsis for the specific patient; and upon a positive prediction of potential late onset neonatal sepsis, manage the delivery of the drug to the specific patient based at least on the prediction of late onset neonatal sepsis.

2. The system of claim 1, wherein the data analysis means is further configured to identify the potential late onset neonatal sepsis based on clinical knowledge data.

3. The system of claim 2, wherein the clinical knowledge data comprises data relating to any one of the following: narcotics provided to one of the one or more patients; surgery undergone by one of the one or more patients; and a clinical condition of the one or more patients.

4. The system of claim 1, wherein the encoded time series data are acquired in real-time.

5. The system of claim 1, further comprising the temporal abstraction analysis being operable to distinguish temporal patterns in the HRV and the RRV scores.

6. The system of claim 1, wherein the one or more medical monitoring devices comprises one or more of: a ECG monitor, and a drug infusion device, and the data analysis means is further operable to analyze the encoded time series data before and after an occurrence of an event to identify differences in temporal patterns caused by the event, and apply the classification matrix to the potential condition onset if the potential condition onset is triggered by the event.

7. The system of claim 1, further comprising a network operable to receive and transfer the analysis data to and from the one or more medical monitoring devices.

8. The system of claim 7, further comprising a web service being operable to receive and transfer the analysis data between the one or more medical monitoring devices and the network.

9. The system of claim 1, further comprising a cloud based environment.

10. A computer-implemented method for providing automated clinical decision support for managing drug delivery to one or more patients based on generated predictions of potential late onset neonatal sepsis in one or more patients estimated based on at least on computational analysis of encoded time series data obtained indicative of one or more relationships between heart rate variability (HRV) scores and respiratory rate variability (RRV) scores, the method comprising:

acquiring time series drug infusion data indicative of one or more characteristics of drug infusion events, and time series heart rate and respiratory rate signals at regular intervals relating to one or more patients from one or more medical monitoring devices, recording the time series heart rate and respiratory signals as the encoded time series data;

analyzing encoded time series data to generate the heart rate variability (HRV) scores and the respiratory rate variability (RRV) scores, the HRV and RRV scores obtained by relations:

$$\forall\, t \in p(t): HRV(t) = \left(\sum_{n=1}^{120} (|HR_n - HR_{n+1}| < \text{th\_HR})\right) \Big/ 2$$

$$\forall\, t \in p(t): RRV(t) = \left(\sum_{n=1}^{120} (|RR_n - RR_{n+1}| < \text{th\_RR})\right) \Big/ 2,$$

where HR is a heart rate for a given point in time, RR is the respiratory rate for the given point in time, th HR is a heart rate threshold, and th_RR is a respiratory rate threshold, the HRV scores and RRV scores each indicative of corresponding numbers of periods of low variability;

applying temporal abstraction analysis to the HRV and the RRV scores to generate analysis data by distinguishing temporal patterns in the HRV and the RRV scores to identify periods of high variability and low variability correlated to the one or more characteristics of the drug infusion events to identify characteristics of physiological responses to the drug infusion events represented in the temporal patterns found in the HRV and RRV scores;

generating or updating a classification matrix based on the distinguished temporal patterns, the classification matrix determined based on one or more identified relationships between the HRV and the RRV scores, the classification matrix maintained in relation to a target demographic population subset receiving similar drug infusion events;

storing the classification matrix in a data structure on a data record associated with the one or more patients;

periodically applying the classification matrix to the HRV and RRV scores, obtained by said relations, of another specific patient to generate a prediction of potential late onset neonatal sepsis for the specific patient; and upon a positive prediction of potential late onset neonatal sepsis, managing the delivery of the drug to the specific patient based at least on the prediction of late onset neonatal sepsis.

11. The method of claim 10, further comprising identifying trends that are temporal patterns in the analysis data, said patterns being characteristic of the potential late onset neonatal sepsis.

12. The method of claim 11, further comprising undertaking analyses of the analysis data to generate indicators of the potential late onset neonatal sepsis in a patient.

13. The method of claim 10, further comprising providing data relating to clinical knowledge.

14. The method of claim 13, wherein the data relating to clinical knowledge comprises any one of the following: narcotics provided to a patient; surgery undergone by the patient, and a clinical condition of the patient.

15. The method of claim 10, further comprising plotting a score of variability relating to the HRV and the RRV scores at regular intervals.

16. The method of claim 10, further comprising setting temporal rules utilized in the determination of the result based on the analysis data.

17. A non-transitory computer readable medium containing computer readable instructions for providing automated clinical decision support for managing drug delivery to one or more patients based on generated predictions of potential late onset neonatal sepsis in one or more patients estimated based on at least on computational analysis of encoded time series data obtained indicative of one or more relationships between heart rate variability (HRV) scores and respiratory rate variability (RRV) scores, wherein the instructions, when executed by a processor, cause the processor to perform steps of:

acquiring time series drug infusion data indicative of one or more characteristics of drug infusion events, and time series heart rate and respiratory rate signals at regular intervals relating to one or more patients from one or more medical monitoring devices, recording the time series heart rate and respiratory signals as the encoded time series data;

analyzing the encoded time series data to generate the heart rate variability (HRV) scores and the respiratory rate variability (RRV) scores, the HRV and RRV scores obtained by relations:

$$\forall\, t \in p(t): HRV(t) = \left(\sum_{n=1}^{120} (|HR_n - HR_{n+1}| < \text{th\_HR})\right) \Big/ 2$$

$$\forall\, t \in p(t): RRV(t) = \left(\sum_{n=1}^{120} (|RR_n - RR_{n+1}| < \text{th\_RR})\right) \Big/ 2,$$

where HR is a heart rate for a given point in time, RR is the respiratory rate for the given point in time, th HR is a heart rate threshold, and th_RR is a respiratory rate threshold, the HRV scores and RRV scores each indicative of corresponding numbers of periods of low variability;

applying temporal abstraction analysis to the HRV and the RRV scores to -generate analysis data by distinguishing temporal patterns in the HRV and the RRV scores to identify periods of high variability and low variability correlated to the one or more characteristics of the drug infusion events to identify characteristics of physiological responses to the drug infusion events represented in the temporal patterns found in the HRV and RRV scores;

generating or updating a classification matrix based on the distinguished temporal patterns, the classification matrix determined based on one or more identified relationships between the HRV and the RRV scores, the classification matrix maintained in relation to a target demographic population subset receiving similar drug infusion events;

store the classification matrix in a data structure on a data record associated with the one or more patients;

periodically applying the classification matrix to the HRV and RRV scores, obtained by said relations, of another specific patient to generate a prediction of potential late onset neonatal sepsis for the specific patient; and upon a positive prediction of potential late onset neonatal sepsis, managing the delivery of the drug to the specific patient based at least on the prediction of late onset neonatal sepsis.

18. The computer readable medium of claim 17, wherein the potential condition is identified based on clinical knowledge data comprising one or more of the following: narcotics provided to one of the one or more patients; surgery undergone by one of the one or more patients, and a clinical condition of the one or more patients.

* * * * *